United States Patent [19]

Ogawa et al.

[11] Patent Number: 5,085,991

[45] Date of Patent: Feb. 4, 1992

[54] PROCESS OF PREPARING PURIFIED AQUEOUS INDOLE SOLUTION

[75] Inventors: Shinji Ogawa, Yokohama; Seiya Iguchi, Mitaka; Hiroshi Kimura; Hideharu Kuwamoto, both of Kamakura, all of Japan

[73] Assignee: Mitsui Toatsu Chemicals, Inc., Tokyo, Japan

[21] Appl. No.: 391,565

[22] PCT Filed: Sep. 22, 1988

[86] PCT No.: PCT/JP88/00968

§ 371 Date: Jul. 21, 1989

§ 102(e) Date: Jul. 21, 1989

[87] PCT Pub. No.: WO89/02923

PCT Pub. Date: Apr. 6, 1989

[30] Foreign Application Priority Data

Sep. 25, 1987 [JP] Japan ................... 62-239001

[51] Int. Cl.$^5$ ..................... C12P 13/22; C07D 209/08
[52] U.S. Cl. ..................... 435/108; 548/469; 548/497
[58] Field of Search ............ 548/469, 497; 435/108

[56] References Cited

U.S. PATENT DOCUMENTS 3,926,726 12/1975 Antonini et al. ............... 435/55

FOREIGN PATENT DOCUMENTS

| 59-62565 | 4/1984 | Japan | 548/469 |
| 61-1129164 | 6/1986 | Japan | 548/469 |
| 63-135369 | 6/1988 | Japan | 548/469 |
| 2151634 | 7/1985 | United Kingdom . | |

OTHER PUBLICATIONS

Won-Gi Bang et al., "Production of L-Tryptophan by Escherichia coli Cells", Biotechnology and Bioengineering, vol. XXV, pp. 999–1011, (1983).

English Language Abstract of Japanese patent 59-11187, published Jan. 20, 1984.

*Primary Examiner*—Mary E. Ceperley
*Attorney, Agent, or Firm*—Burns, Doane, Swecker & Mathis

[57] ABSTRACT

A process for preparing substantially purified aqueous indole solution. In the process of the present invention, crude indole containing an organic impurity is dissolved in an organic solvent which is immiscible with water, the distribution ratio of the impurity to the organic phase, when two-phase liquid system is formed with the organic solvent and an aqueous medium, being greater than that of indole; and the indole solution is contacted with water or an aqueous reaction medium for conducting the reaction to form two-phase liquid system and to distribute indole to the aqueous phase.

6 Claims, No Drawings

PROCESS OF PREPARING PURIFIED AQUEOUS INDOLE SOLUTION

BACKGROUND OF THE INVENTION

This invention relates to a process of preparing purified aqueous indole solution. More particularly, this invention relates to a process of preparing substantially purified aqueous indole solution from crude indole containing an organic impurities.

A number of methods are known for synthesizing useful compounds by an enzyme reaction employing indole as substrate of the enzyme. A typical example of such a method is a process of synthesizing L-tryptophan from indole and L-serine using tryptophan synthase, and this process is now industrially practiced.

In general, indole is produced by a chemical synthesis process or by fractional distillation of coal tar, and indole produced by such a process usually contains substituted indoles such as ethylindole and other aromatic compounds as impurities. Some of these impurities inhibit or even completely deactivate the enzyme if they exist in the reaction mixture. Therefore, in order to conduct the enzyme reaction fluently, these impurities should not exist in the reaction mixture and should not be accumulated in the reaction mixture.

On the other hand, for most of the enzymes which are used in enzyme reactions, water acts as an ideal solvent. Therefore, in most cases, the enzyme reaction is conducted in aqueous solution. Further, since most enzymes exhibit high activity at a temperature of 15° C. to 50° C., enzyme reactions are usually conducted in this temperature range.

However, indole is insoluble in water and its solubility in water at room temperature is only 3–4 g/l. Therefore, in an enzyme reaction in which indole is used as a starting material, it is not easy to prepare and supply aqueous indole solution, especially quantitatively.

Conventional methods of preparing aqueous indole solution include a method in which solid indole powder is dissolved in water or in aqueous solution which already contains indole by vigorous agitation to prepare aqueous indole solution, and the undissolved indole is recovered by separating solid from liquid, and a method in which indole solution is prepared by dissolving indole in a solvent which is miscible with water such as lower aliphatic alcohol, e.g., methanol, and the indole solution is then mixed with aqueous indole solution.

By these methods, the quantitativeness of the indole concentration in the aqueous solution is assured However, when industrially produced crude indole is used, the impurities contained therein are also dissolved in the aqueous solution and are supplied to the enzyme reaction. Thus, when crude indole is used in the above-mentioned conventional methods, purification of the indole is not performed, so that it is not preferred for use in the enzyme reaction. Further, in cases where a solvent miscible with water is used, the solvent per se denatures, inhibits or deactivates the enzyme, so that the use of such a solvent should be avoided.

As an enzyme reaction in which indole is a substrate, a method using an organic solvent in the reaction has been proposed.

That is, Japanese Patent Publication No. 45593/81 discloses to conduct an enzyme reaction in which the substrate of the enzyme is almost insoluble in the enzyme-containing solution, in the presence of an organic solvent which is immiscible with water but miscible with the substrate. However, in this method, the function of the organic solvent is to assure the substrate in substantially the same concentration as the saturated concentration thereof in the aqueous phase in which the reaction by enzyme is conducted.

Japanese Patent Disclosure (Kokai) No. 11187/84 discloses that in an enzyme reaction in which at least one substrate inhibits the enzyme activity, an organic solvent which is immiscible with water but miscible with the substrate is added so as to reduce the substrate concentration in the aqueous phase to a level at which the enzyme activity is not inhibited. In this reference, a method of enzymatically synthesize L-tryptophan using indole as a substrate is disclosed.

Further, Bang et al disclose a method of synthesizing L-tryptophan from indole and L- or DL-serine using E. coli cells, in which indole is dissolved in an organic solvent immiscible with water and the indole solution is used as a source of indole in the enzyme reaction. (Biotechnology and Bioengineering. vol. XXV 999-1011, 1983).

These methods in which an organic solvent which is immiscible with water is used are effective methods in the case where a substance such as indole which is substantially insoluble in water is a substrate of an enzyme. However, these methods do not care at all about the impurities contaminated in indole, and they intend to employ pure indole. Therefore, in these methods, the role of the organic solvent is only to restore indole and supply it to the aqueous phase at a fixed concentration when conducting an enzyme reaction.

However, in cases where the indole which is used as a starting material is crude indole containing the organic impurities, care should be taken for the selection of the organic solvent. The present inventors found that o-ethylaniline or 3-methylindole which may be contained in the crude indole inhibits the enzyme, tryptophan synthase which synthesize tryptophan from indole and L-serine at a level of about 200 ppm, and 2-ethylindole inhibits the enzyme at a level of as low as about 20 ppm. There are some other impurities which inhibit the enzyme if they exist at a high level of 1000 ppm or more.

Thus, even if the organic solvent which is immiscible with water restores indole and assures to supply indole in the aqueous phase at a constant concentration, if the organic impurities are distributed to the aqueous phase to the same degree as indole, the impurities co-exist in the enzyme reaction system to inhibit the enzyme. Further, even if an organic solvent of which distribution ratio of the impurities is somewhat lower than that of indole is employed, since the substrate indole is consumed by the enzyme reaction while the impurities are usually not consumed in the reaction, the impurities accumulate in the reaction system. Thus, if an organic solvent with a distribution ratio of the impurities to the aqueous phase of not sufficiently small is employed, it is not easy to prevent the inhibition of the enzyme reaction or the contamination of the product of the enzyme reaction, so that it is difficult to conduct the enzyme reaction fluently.

However, no finding or consideration is disclosed in the prior art in which the organic solvent which is immiscible with water is employed. As a countermeasure for solving the problem of the contaminating impurities, to purify the crude indole is considered. However, although indole may be purified by rectification or recrystallization, most of the contained impurities are substituted derivatives of indole with physiological properties similar to those of indole, so that the purity of indole which may be attained by the purification operation such as rectification is limited. Among the purification operations, recrystallization is a suitable method for obtaining indole with high purity. However, the recovery of indole is low, and the operation has a problem in the accumulation of the impurities in the filtrate Further, the cost for conducting recrystallization is high. Thus, for industrial production, a process of purification without recrystallization is demanded.

SUMMARY OF THE INVENTION

The object of the present invention is to provide a process of preparing substantially purified aqueous indole solution from crude indole containing organic impurities, which indole solution can be used for an enzyme reaction in which indole is used as a starting material.

Another object of the present invention is to provide an industrial method for conducting an enzyme reaction in which indole is used as a starting material, in which purified indole solution from which impurities inhibiting the enzyme reaction is removed is supplied to the aqueous reaction system containing the enzyme.

The objects of the present invention may be accomplished by providing a process of preparing substantially purified aqueous indole solution comprising the steps of preliminarily dissolving crude indole containing organic impurities in an organic solvent which is immiscible with water, the distribution ratio of the impurity to the organic phase, when two-phase liquid system is formed with the organic solvent and an aqueous medium, being greater than that of indole, and contacting the organic indole solution with water or an aqueous reaction medium for conducting the reaction to form two-phase liquid system and to distribute indole to the aqueous phase.

The present inventors found that impurities which inhibit the enzyme activity are contained in crude indole synthesized by a chemical synthesis process. In the process of the present invention, unlike the prior art method in which indole is isolated by the above-mentioned complicated purification operation and is supplied to the reaction, crude indole is used as a starting material and purified aqueous indole solution is prepared by a simple process and is supplied to the reaction system containing the enzyme as purified indole.

Conventionally, in an enzyme reaction in which indole is a substrate of the enzyme, in order to obtain a purified aqueous indole solution for supplying to the reaction system, it was necessary to preliminarily prepare purified indole by rectification or recrystallization operation and to prepare purified aqueous indole solution. In contrast, by the process of the present invention, not only purified aqueous indole solution can be prepared from industrially available crude indole with low purity using the crude indole as a starting material as it is, but also aqueous indole solution with a desired indole concentration can be prepared easily and quantitatively.

Therefore, the process of the present invention has a high industrial value as a method in which enzyme reaction can be conducted using crude indole as a starting material, which is produced by chemical synthesis or the like.

It should be noted, however, although the process of the present invention is most advantageous when employed in a reaction such as an enzyme reaction in which the contamination of the organic impurities gives a problem, the process of the present invention is not restricted to be applied to such an enzyme reaction and can be applied to other reactions for producing dyes or various other substances, in which indole is used as a starting material.

BEST MODE FOR CARRYING OUT THE INVENTION

The crude indole used in the process of the present invention includes, for example, those chemically synthesized by reacting anilines and ethyleneglycols under the presence of various catalysts, by catalytic reaction of anilinoethanol and o-nitrotoluene or the like, and by the dehydration reaction of indoline, as well as those obtained by fractional distillation of coal tar. The organic impurities contained in the crude indole obtained by these processes include, for example, substituted indoles such as 2-methylindole, 3-methylindole, N-methylindole, 2-ethylindole, 3-ethylindole and N-ethylindole; cyclic compounds such as 2-methylquinoline and N-phenylpyrrole; substituted anilines and derivatives such as aniline, o-ethylaniline, N-ethylaniline and acetaldehydeanil; o-toluidine; and anilinoethanol.

The organic solvent for dissolving the crude indole containing such organic impurities is one which is immiscible with water, which forms two-phase system when mixed with water, and which can dissolve indole. In order that the organic solvent does not inhibit the enzyme reaction, those solvents of which solubility in water is very small is preferred irrespective of whether the solvent is aliphatic or aromatic. Preferred examples of the organic solvents include saturated aliphatic hydrocarbons such as pentane, n-hexane, heptane, isooctane and nonane; cycloaliphatic hydrocarbons such as cyclohexane and methylcyclohexane; aromatic hydrocarbons such as benzene, toluene and xylene; esters such as butyl acetate, butyl citrate and ethyl citrate; and ketones such as methylisobutyl ketone and diisobutyl ketone. Among these, aliphatic solvents are more preferred than aromatic solvents because the denaturation and inhibition of the enzyme is smaller.

Further, in order to obtain substantially purified aqueous insole solution, an organic solvent which the affinity of the impurities thereto is different from that of indole is selected. That is, an organic solvent with a distribution ratio of the impurities to the organic phase, when two-phase system is formed with the organic solvent and an aqueous medium, which is greater than that of indole is selected. As mentioned above, the organic impurities contained in the crude indole industrially produced by chemical synthesis or the like have melting point or boiling point which is different from that of indole. In order to largely differentiate the distribution ratio of the impurities and indole utilizing such differences, an organic solvent which at least has a high solubility of the impurities is selected. Thus, those solvents which have a solubility parameter of 7-9.5 at the temperature at which the reaction is conducted are preferably selected. Further, depending on the organic impurities contained in the crude indole, more suitable organic solvent can be selected. That is, in cases where the crude indole contains impurities such as 2-methylindole and 3-methylindole of which both the melting point and the boiling point are higher than those of indole, those solvents with a solubility parameter (SP) of about 8, such as methylcyclohexane and cyclohexane are preferred, while in cases where the crude indole contains impurities such as 2-ethylindole and 3-ethylindole of which melting point is lower than that of indole, those solvents with a SP of about 7, such as n-hexane and isooctane can give satisfactory purification effect. An appropriate solvent can be selected in the industrial process actually conducted considering the influence of the solvent to the enzyme reaction, the ease of handling thereof and the like.

The purified aqueous indole solution can be prepared by dissolving the crude indole in the above-described organic solvent and then contacting the organic indole solution with water. The water may be mere water containing nothing but may contain all or a part of the other substrates and/or inorganic salts which may be necessary for conducting the enzyme reaction. Further, if the use of the organic solvent does not give an inhibition to the activity of the enzyme, an enzyme source, that is, free enzyme or bacterial cell producing the enzyme, as well as those immobilized in a carrier may be present in the water.

The crude indole is dissolved in the above-described organic solvent and the resulting solution is contacted and mixed with water or an aqueous solution containing a substrate or the like which is necessary for the reaction. Based on the difference between the distribution coefficient of indole and the organic impurities between organic-aqueous phases, almost all the impurities are retained in the organic layer and are not transferred to the aqueous phase, so that the aqueous phase becomes substantially purified aqueous indole solution which does not substantially contain the impurities. Further, if necessary, the mixed solution can be supplied to the enzyme reaction after separating the organic and aqueous phases by leaving to stand the mixture.

The method of contacting and mixing the organic solvent phase and the aqueous phase is not restricted. Apparatuses such as a stirred tank or static mixer which are usually used in liquid-liquid extraction may be employed. To promote the transferring rate between the organic and aqueous phases, apparatuses in which the liquid-liquid interface area is large are preferred. Further, if necessary, the separation of the phases by settlement can also be conducted in a conventional liquid-liquid extraction device.

Further, it is also a characteristic feature of the present invention that aqueous indole solution with a desired indole concentration can quantitatively be prepared by appropriately selecting the concentration of the crude indole dissolved in the organic solvent, the volume ratio of the organic and aqueous phases, the temperature and the duration of contact when the organic solution is contacted and mixed with the aqueous medium.

Needless to say, additional crude indole can be added to the organic solvent phase after separation by settlement to adjust the indole concentration and then reuse the organic solvent for contacting and mixing with the aqueous medium. Although if the organic solvent is repeatedly reused as mentioned above, the organic impurities accumulate in the organic solvent, if necessary, indole contained in the organic solvent can be recovered by distillation or recrystallization and the recovered indole can be reused for preparing the purified aqueous indole solution in accordance with the present invention.

The present invention will now be described in more detail referring to the examples thereof. Needless to say, the invention is not limited to the examples.

EXAMPLE 1

Ten grams of crude indole powder with a purity of 98.5% by weight containing as impurities 2-methylindole, 3-methylindole, N-ethylindole and aniline was dissolved in 50 ml of toluene (with SP value of 8.9). The thus obtained solution and 50 ml of distilled water were introduced in a separating funnel and the resulting mixture was shaken for 10 minutes at 30° C. The mixture was then left to stand to separate the organic and the aqueous phases. The concentrations of indole and the impurities in the aqueous phase were determined. The concentration of indole was 2.0 g/l and the percentage of indole in all of the organic components in the aqueous phase was 99.9% by weight. The same crude indole was dissolved in 50 ml of tert-butyl alcohol (with SP value of 11 0) in the same amount and the same operation was conducted. As a result, the concentration of indole in the aqueous phase was 5.9 g/l and the percentage of indole in the aqueous phase was 98.9% by weight.

EXAMPLE 2

In 500 ml of n-hexane (with SP value of 7.3), 16 g of crude indole with a purity of 97.5% by weight containing the same impurities as in Example 1 was dissolved and the resulting solution was contacted and mixed with 500 ml of aqueous solution containing 7.5 g of L-serine The resulting mixture was separated by settlement. The indole concentration in the resulting aqueous phase was 1.9 g/l, and the ratio of indole to the impurities originated from indole was 99.8% by weight to 0.2% by weight. The concentration of L-serine in the aqueous phase was not changed before and after the operation. Further, the concentration of n-hexane in the aqueous phase was 10 ppm.

EXAMPLE 3

To 15 g of indole for producing perfume, which consists of 99.95% by weight of indole and 0.05% by weight of 3-methylindole, prescribed amount of 3-methylindole with 99.9% by weight purity was blended to prepare indole with various purities. The thus prepared indole was dissolved in 90 ml of n-hexane and the solution was contacted and mixed with 210 ml of aqueous solution containing 2.8 g of L-serine, 1.0 g of glycine, 0.1 g of calcium chloride dihydrate and 2 mg of pyridoxal-5'-phosphate, of which pH was adjusted to 8.5 with aqueous ammonia. The organic phase and the aqueous phase was separated by settlement and the concentrations of indole and 3-methylindole were analyzed by high performance liquid chromatography. The weight ratio of the indole to 3-methylindole dissolved in n-hexane before the contact with the aqueous medium and that in the aqueous phase after the contact are summarized in Table 1.

TABLE 1

| Organic Phase Before Contact | | Aqueous Phase After Contact | |
| --- | --- | --- | --- |
| Indole | 3-methylindole | Indole | 3-methylindole |
| 98.5% by weight | 1.5% by weight | 99.7% by weight | 0.3% by weight |

TABLE 1-continued

| Organic Phase Before Contact | | Aqueous Phase After Contact | |
| --- | --- | --- | --- |
| Indole | 3-methylindole | Indole | 3-methylindole |
| 94.0% by weight | 6.0% by weight | 98.5% by weight | 1.5% by weight |
| 90.0% by weight | 10.0% by weight | 97.6% by weight | 2.4% by weight |
| 80.0% by weight | 20.0% by weight | 94.5% by weight | 5.5% by weight |

REFERENCE EXAMPLE 1

*Escherichia coli* MT-10232 (FERM BP-19), which is a tryptophan synthase-producing bacterium, was inoculated to 100 ml of the culture medium having the composition shown in Table 2 in a 500 ml flask, and was incubated at 35° C. for 24 hours. Two hundred milliliters (in two flasks) of the culture medium was inoculated to 15 l of the culture medium having the composition shown in Table 3 in 30 l of jar fermenter and was incubated at 35° C., pH 6.8 (adjusted with 28% aqueous ammonia) for 30 hours.

After the culture, the culture medium was centrifuged to collect 600 g wet weight of the bacterial cells. The cells were placed in a sealed container and restored in a refrigerator at 4° C., and were used for preparing the immobilized enzyme source.

TABLE 2

| | |
| --- | --- |
| Ehrlich's Meat Extract | 10 g |
| Polypeptone | 10 g |
| NaCl | 5 g |
| Dissolved in 1 liter of distilled water (pH 6.8) | |

TABLE 3

| Composition of Growth Medium | |
| --- | --- |
| Glucose | 10 g |
| $(NH_4)_2SO_4$ | 1.5 g |
| $K_2HPO_4$ | 1 g |
| $MgSO_4.7H_2O$ | 1 g |
| Polypeptone | 0.5 g |
| Yeast Extract | 0.5 g |
| L-tryptophan | 0.15 g |
| Surfactant (Adecanol LG-805, manufactured by Asahi Denka Co., Ltd.) | 5 g |
| Dissolved in 1 liter of distilled water (pH 6.8) | |

One part of the above-described wet bacterial cells and one part of isotonic sodium chloride solution were mixed with stirring. On the other hand, 7.76 parts of distilled water and 0.24 parts of sodium alginate (NSPLL manufactured by Kibun Food Chemifa, Co., Ltd.) were mixed with stirring and pH thereof was adjusted to 8.5 with sodium hydroxide.

Two parts of the suspension of the cells and 8 parts of the sodium alginate solution were mixed with stirring and the resulting mixture was fed into a syringe and was dropped into a gelling solution from the tip of a needle with an inner diameter of 0.5 mm to 0.8 mm.

The gelling solution was 0.5 M aqueous calcium chloride dihydrate solution of which pH was adjusted to 8.5 with 6 N potassium hydroxide solution, kept at 10° C., and was used in the amount of 10 parts.

The particles formed by dropping the mixture into the gelling solution was matured under stirring in the gelling solution to obtain immobilized enzyme source.

To each of the aqueous solutions with a volume of 100 ml containing aniline, N-ethylaniline, o-ethylaniline, o-toluidine, 3-methylindole or 2-ethylindole in the amount shown in Table 4, 0.15 g of calcium chloride dihydrate and 1 mg of pyridoxal-5'-phosphate were added, and the pH thereof was adjusted to 8.5 with aqueous ammonia.

In these aqueous solutions, 5 g of the above-described immobilized enzyme source containing the tryptophan synthase-producing bacteria was added and the mixtures were left to stand at 30° C. Further, as a reference solution, 100 ml of distilled water containing no organic substance was subjected to the same procedure as described above and the immobilized enzyme source was added thereto as mentioned above, followed by being left to stand at 30° C.

Twenty four hours later and 96 hours later, 1 g of immobilized enzyme source was removed from each of the solutions and the enzyme activity was determined. The ratio of the activity of the enzyme left in the solution of the organic substance to the activity of the enzyme left in the reference solution was determined and is shown in Table 4.

The enzyme activity was determined as follows:

Ten milliliters of reaction medium containing indole, L-serine, pyridoxal-5'-phosphate (PLP) and 0.3 g of the immobilized enzyme source was prepared and the reaction was conducted at 35° C. in a shaking incubator for 1 hour with shaking. The produced L-tryptophan was analyzed with high performance liquid chromatography.

TABLE 4

| Organic Impurity | Concentration ppm | Activity Ratio | |
| --- | --- | --- | --- |
| | | 24 Hours Later | 96 Hours Later |
| Aniline | 200 | 0.98 | 1.01 |
| | 1000 | 1.00 | 0.82 |
| N-ethylaniline | 200 | 1.04 | 0.97 |
| | 1000 | 1.00 | 0.89 |
| o-ethylaniline | 200 | 0.90 | 0.77 |
| | 1000 | 0.71 | 0.50 |
| o-toluidine | 200 | 0.97 | 1.06 |
| | 1000 | 0.88 | 0.80 |
| 3-methylindole | 200 | 0.94 | 0.89 |
| | 500 | 0.94 | 0.84 |
| 2-ethylindole | 20 | 0.93 | 0.71 |
| | 50 | 0.73 | 0.54 |
| | 200 | 0.68 | 0.48 |

EXAMPLE 4

In a continuous stirred tank reactor containing an immobilized enzyme source, enzyme reaction was conducted using crude indole and purified indole solution and the half life of the enzyme activity was compared. An aqueous solution containing 10.0 g/l of L-serine, 1.5 g/l of calcium chloride dihydrate and 10 mg/l of pyridoxal-5'-phosphate, of which pH was adjusted to 8.5 with aqueous ammonia (hereinafter referred to as solution A) was supplied to the reaction. In each of three 500 ml glass reactors with a stirrer, 100 ml of the above-described solution A and 30 g of immobilized enzyme source containing the tryptophan synthase-producing cells were placed and the reactors were held in warm water to keep the temperature at 35° C.

To the first reactor, the solution A was supplied at a rate of 49 ml per hour. On the other hand, a crude indole containing 94.0% by weight of indole and 6.0% by weight of 3-methylindole was dissolved in 70 vol% aqueous methanol solution to prepare an aqueous solution with an indole concentration of 75 g/l and 3-methylindole concentration of 4.79 g/l. This solution was continuously supplied to the reactor at a rate of 1 ml per hour. Further, the reaction mixture was drawn from the reactor at a rate of 50 ml per hour to perform continuous synthesis reaction of L-tryptophan. Aliquote of the reaction mixture was sampled at fixed time, and the concentration of 3-methylindole and L-tryptophan were determined with high performance liquid chromatography. After 24 hours from the start of supplying the indole solution, the concentration of 3-methylindole was 96 mg/l. The yield of the L-tryptophan with respect to the supplied indole in a unit time was determined. The time from the beginning of the reaction at which the yield is reduced to 50%, i.e., the half life of the enzyme activity was 615 hours.

On the other hand, the crude indole having the same composition was dissolved in n-hexane and was contacted and mixed with the solution A as in Example 3. After separation by settlement, purified aqueous indole solution (solution B) was obtained. In the second reactor, the solution B was supplied at a rate of 50 ml per hour and the reaction mixture was continuously drawn at the same rate. The concentration of 3-methylindole in the reaction mixture was 19 mg/l. The half life of the enzyme activity was 960 hours.

Further, in the third reactor, the continuous enzyme reaction was conducted in the same manner as in the first reactor except that indole for producing perfume consisting of 99.95% by weight of indole and 0.05% by weight of 3-methylindole was used. The concentration of 3-methylindole in the reaction mixture was 0.7 mg/l, and the half life of the enzyme activity was 1070 hours.

The amount of indole supplied to each reactor per 1 hour was uniformly 75 mg.

INDUSTRIAL APPLICABILITY

The process of the invention can be applied for enzyme reactions or reactions which do not use an enzyme, for producing tryptophan, dyes or various other substances.

We claim:

1. A process of preparing L-tryptophan comprising the steps of:
   (i) dissolving a crude indole containing an organic impurity in an organic solvent which is immiscible with water, the distribution ratio of the impurity to the organic phase, when a two-phase liquid system is formed with the organic solvent and an aqueous medium, being greater than that of indole;
   (ii) separating the impurity from the indole by contacting the organic indole solution with an aqueous reaction medium containing L-serine substantially in the absence of tryptophan synthase to form a two-phase liquid system, the first phase of the liquid system being an aqueous phase having the indole distributed therein, and the second phase being an organic phase containing the organic impurity;
   (iii) collecting said aqueous phase to obtain an aqueous solution containing indole and L-serine; and
   (iv) contacting said aqueous solution containing indole and L-serine with immobilized tryptophan synthase.

2. A process for preparing in a substantially purified aqueous indole solution comprising the steps of:
   (i) dissolving a crude indole containing an organic impurity in an organic solvent which is immiscible with water, the distribution ratio of the impurity to the organic phase, when a two-phase liquid system is formed with the organic solvent and an aqueous medium, being greater than that of indole; and then
   (ii) contacting the organic indole solution with an aqueous reaction medium containing L-serine substantially in the absence of tryptophan synthase to form a liquid system comprising two phases, the first phase of the liquid system being an aqueous phase having the indole distributed therein, and the second phase being an organic phase containing the organic impurity; and then
   (iii) separating the impurity from the indole by recovering the first phase having the indole distributed therein from the liquid system.

3. The process of claim 2, wherein the organic impurity is aniline, N-ethylaniline, o-ethylaniline, o-toluidine, 3-methylindole or 2-ethylindole.

4. The process of claim 2, wherein the solubility parameter of the organic solvent at the temperature of performing the reaction is 7-9.5.

5. The process of claim 2, wherein the organic solvent is n-hexane.

6. The process of claim 1, wherein the organic impurity is aniline, N-ethylaniline, o-ethylaniline, o-toluidine, 3-methylindole or 2-ethylindole.

* * * * *

UNITED STATES PATENT AND TRADEMARK OFFICE
CERTIFICATE OF CORRECTION

PATENT NO. : 5,085,991

DATED : February 4, 1992

INVENTOR(S) : Ogawa et al.

It is certified that error appears in the above-identified patent and that said Letters Patent is hereby corrected as shown below:

In column 10, line 21, delete "in".

Signed and Sealed this

Seventeenth Day of August, 1993

Attest:

BRUCE LEHMAN

Attesting Officer

Commissioner of Patents and Trademarks